United States Patent [19]

Blattner

[11] 4,112,110
[45] Sep. 5, 1978

[54] OXYGENATED AZATETRACYCLIC COMPOUNDS

[75] Inventor: Hans Blattner, Riehen, Switzerland

[73] Assignee: Ciba-Geigy Corporation, Ardsley, N.Y.

[21] Appl. No.: 738,498

[22] Filed: Nov. 3, 1976

Related U.S. Application Data

[63] Continuation of Ser. No. 549,628, Feb. 13, 1975, abandoned.

[30] Foreign Application Priority Data

Feb. 22, 1974 [CH] Switzerland .................. 2545/74

[51] Int. Cl.$^2$ ............... C07D 491/06; H61K 31/40
[52] U.S. Cl. ........................ 424/274; 260/326.28; 260/326.29; 260/326.5 B; 260/326.55 A; 260/327 R; 260/333
[58] Field of Search ............. 260/326.9, 326.5 B, 260/326.28, 326.29, 326.55 A; 424/474

[56] References Cited

U.S. PATENT DOCUMENTS 3,636,045  1/1972  Blattner et al. ............ 260/326.5 B
3,636,046  1/1972  Blattner et al. ............ 260/326.5 B Primary Examiner—Donald G. Daus
Assistant Examiner—M. Vaughn
Attorney, Agent, or Firm—John J. Maitner

[57] ABSTRACT

5-Oxygenated azatetracyclic compounds of the formula

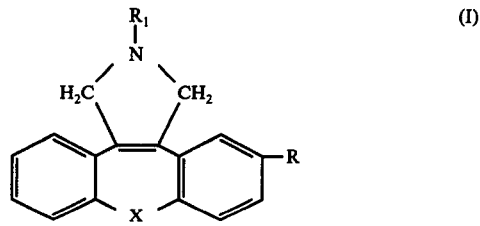

wherein X represents oxygen or sulphur, R represents a hydroxy group optionally esterified by an alkanecarboxylic acid, and $R_1$ stands for a lower alkyl, lower alkenyl or allyl, or salts thereof, such compounds having a central-depressant and agitation-inhibiting action connected with cataleptic effects to a very low extent only these properties rendering the new compounds suitable as tranquillizing, antipsychotic and agitation-inhibiting substances.

18 Claims, No Drawings

OXYGENATED AZATETRACYCLIC COMPOUNDS

This is a continuation of application Ser. No. 549,628 filed Feb. 13, 1975, now abandoned.

This invention relates to new azatetracyclic compounds, particularly to 5-oxygenated 2,3-dihydro-1H-dibenzo [2,3:6,7]thiepino[4,5-c]pyrrole compounds, substituted in the 1-position, of the formula

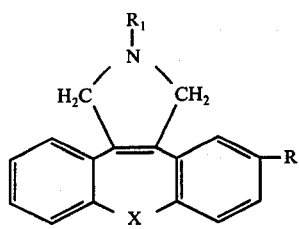

wherein X represents oxygen or sulphur, R represents a hydroxy group optionally esterified by an alkane-carboxylic acid, and $R_1$ stands for lower alkyl or lower alkenyl, and to salts of such compounds, as well as to processes for the production thereof, to pharmaceutical preparations containing the new compounds and to the use thereof.

The group R represents in the first place hydroxy; it can, however, also be alkanoyloxy, wherein alkanoyl stands for the acyl radical of an alkanecarboxylic acid preferably having up to 20 carbon atoms, and represents, e.g., loweralkanoyl having up to 7 carbon atoms, such as acetyl, propionyl, butyryl, pivaloyl, caproyl or heptanoyl, or higher-alkanoyl having 8 to 20 carbon atoms, such as undecanoyl, lauroyl, myristoyl, palmitoyl, stearoyl or arachidoyl.

A lower alkyl group $R_1$ has up to 7, preferably up to 4, carbon atoms and is, e.g., methyl, ethyl, n-propyl, isopropyl, n-butyl, isobutyl or tert.-butyl, also straight-chain or branched-chain pentyl, hexyl or heptyl bound in any position.

A lower alkenyl group $R_1$ has up to 7, preferably up to 4, carbon atoms and is, e.g., 2-lower-alkenyl such as allyl or methallyl.

Salts of compounds of formula I are, in particular, acid addition salts, especially pharmaceutically applicable nontoxic acid addition salts, e.g. with inorganic acids such as hydrochloric acid, hydrobromic acid, sulphuric acid or phosphoric acid, or with organic acids, such as organic carboxylic and sulphonic acids such as methanesulphonic acid, ethanesulphonic acid, 2-hydroxyethanesulphonic acid, acetic acid, malic acid, tartaric acid, citric acid, lactic acid, oxalic acid, succinic acid, fumaric acid, maleic acid, benzoic acid, salicyclic acid, phenylacetic acid, mandelic acid or embonic acid.

The new compounds have valuable pharmacological properties, e.g. properties affecting the central nervous system. They are characterised above all by their central-depressant action and agitation-inhibiting action (amphetamine-antagonistic), which can be demonstrated by pharmacological tests. They thus exhibit in the amphetamine-antagonism test (Niemegeers and Janssen, Arzneimittelforsch., Vol. 24, p. 45 (1974)) on the rat an agitation-inhibiting action in a dosage range of 3 to 10 mg/kg subcutaneously, or 10 to 40 mg/kg orally. At the same time, in the catalepsy test on the rat (Wirth et al., Arch. Int. Pharmacodyn., Vol. 115, p. 1 (1958), it is only with oral administration of doses as high as about 20 to 100 mg/kg that the new compounds show cataleptic effects; the relationship between cataleptic (extrapyramidal) action and amphetamine-antagonistic action is therefore favourable with respect to the agitation-inhibiting action. The new compounds can thus be used as tranquillising, antipsychotic and agitation-inhibiting compounds for the treatment of conditions of tension and agitation.

The invention relates foremost to compounds of formula I wherein X stands for sulphur, as well as for oxygen, R for hydroxy, as well as for lower alkanoyloxy having up to 7 carbon atoms, e.g. acetyloxy, propionyloxy, pivaloyloxy, caproyloxy or heptanoyloxy, and also higher alkanoyloxy having 8–20 carbon atoms, e.g. lauroyloxy, myristoyloxy, palmitoyloxy or stearoyloxy, and $R_1$ for lower alkyl having up to 4 carbon atoms, e.g. methyl or ethyl, as well as allyl; it relates especially to the compounds given in the examples, or salts thereof, particularly acid addition salts, such as pharmaceutically applicable nontoxic acid addition salts thereof.

The new compounds can be produced in a manner known per se. They are obtained, for example, by a process in which a compound of the formula

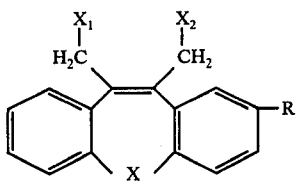

wherein $X_1$ and $X_2$ represent reactive esterified hydroxy groups, is reacted with an amine of the formula $$R_1-NH_2 \qquad (III)$$

and, optionally, in a resulting compound of formula I, the group R is converted into another group R, and/or, optionally, a resulting salt is converted into the free compound or into another salt, or a free compound obtained is converted into a salt.

A reactive esterified hydroxy group $X_1$ or $X_2$ is a hydroxy group esterified with a strong acid of inorganic or organic character, such as a hydroxy group esterified with a mineral acid, e.g. a hydrohalic acid such as hydrochloric acid, hydrobromic acid or sulphuric acid, or with a strong organic sulphonic acid, e.g. an aliphatic or aromatic sulphonic acid such as methanesulphonic acid, p-toluenesulphonic acid, 4-bromobenzenesulphonic acid or 4-nitrobenzenesulphonic acid. $X_1$ or $X_2$ stands, in particular, for halogen, especially for bromine; it can however also represent organic sulphonyloxy, e.g. p-toluenesulphonyloxy.

The reaction of the starting material of formula II with the amine of formula III is usually performed in the presence of a basic agent, preferably an excess of the amine of formula III, but also in the presence of an additional inorganic or organic base, and preferably in the presence of a solvent or diluent, particularly one that is inert to the reactants under the reaction conditions, e.g. an aliphatic, cycloaliphatic or aromatic hydrocarbon such as benzene or toluene, a halogenated aliphatic, cycloaliphatic or aromatic hydrocarbon such as chloroform, a lower alkanol such as methanol or ethanol, an ether such as diethyl ether or dioxane, a lower alkanone such as acetone, methyl ethyl ketone or diethyl ketone, or a nitrile such as acetonitrile, or a mixture of such solvents, especially a mixture of a lower alkanol and a hydrocarbon, e.g. benzene. The reaction is performed if necessary with cooling or heating, e.g. in a temperature range of about −10° C to about +50° C, in a closed vessel and/or in an inert gas atmosphere, e.g. in a nitrogen atmosphere.

The starting materials of formula II can be produced in a manner known per se, e.g. by a process in which a 2-(4-$R_A$-phenyl-X-)-phenylacetic acid, wherein $R_A$ denotes a suitably protected hydroxy group, e.g. a suitably esterified hydroxy group, such as one esterified by the acyl radical of a carbonic acid semi-ester, or an etherified hydroxy group, such as one etherified by a lower alkyl radical or 2-oxocycloalkyl radical, is converted into an ester such as a lower alkyl ester, e.g. methyl or ethyl ester; and this is condensed, in the presence of an alkali metal such as sodium, with a di-lower alkyl carbonate, e.g. diethyl carbonate, to the di-ester of the corresponding 2-(4-$R_A$-phenyl-X-)-phenylmalonic acid. This is methylated in the α-position in the usual manner, e.g. by treatment with a metallising reagent such as an alkali metal lower alkanolate, alkali metal amide or alkali metal hydride, and reaction with a reactive ester of methanol, such as with a methyl halide, e.g. methyl iodide. The malonic ester compound is then converted, with simultaneous decarboxylation, into the corresponding 2-(4-$R_A$-phenyl-X-)-hydratropic acid. This yields, with the action of a suitable acid reagent such as hydrofluoric acid, a 11-methyl-10-oxo-10,11-dihydrodibenzo[b,f]thiepin or an 11-methyl-10-oxo-10,11-dihydro-dibenzo[b,f]oxepin, which contains in the 8-position, depending on the meaning of the group $R_A$ present in the starting material, the group $R_A$ or a hydroxy group liberated under the reaction conditions; the last-mentioned is converted back, in a manner known per se, into a suitably protected hydroxy group $R_A$. The keto compound obtained in this manner is subsequently treated with a suitable methyl Grignard's reagent such as methyl magnesium iodide; water is then split off from the resulting 8$R_A$-10,11-dimethyl-10-hydroxy-10,11-dihydrodibenzo[b,f]thiepin or -dibenzo[b,f]oxepin, e.g. by heating in the presence of aqueous mineral acid such as hydrochloric or sulphuric acid; and the 8-$R_A$-11-methyl-10-methylene-10,11-dihydro-dibenzo[b,f]thiepin compound or -dibenzo[b,f]oxepin compound obtainable as the main product is converted, e.g. by treatment with a suitable base such as an alkali metal hydroxide, e.g. potassium hydroxide, in the presence of a lower alkanol, e.g. ethanol, to the corresponding 8-$R_A$-10,11-dimethyl-dibenzo[b,f]thiepin or -dibenzo[b,f]oxepin. The methyl groups in this are converted into the reactive esterified hydroxymethyl groups of the formula $X_1$—$CH_2$— or $X_2$—$CH_2$—, e.g. by treatment with a positive halogen-releasing agent such as an N-halogen-imide, e.g. bromosuccinimide. In an 8-$R_A$-10,11-bis-halomethyl-dibenzo[b,f]thiepin or -dibenzo[b,f]oxepin obtainable in this manner, halogen, especially bromine, can be converted in a manner known per se, e.g. with formation and subsequent esterifying of hydroxyl groups, into another reactive esterified hydroxy; furthermore, the protected hydroxy group $R_A$ can be converted in a manner known per se, e.g. as described below, at this preliminary stage or at some other suitable one, into the group R.

The new compounds can be obtained also by substituting in a compound of the formula

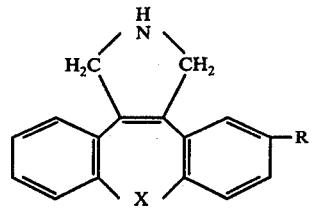

the secondary amino group by the group $R_1$, and, optionally, carrying out the additional stages of the process.

The substitution of the N-unsubstituted starting material of formula IV is performed in a manner known per se, e.g. by treatment with a reactive ester of a lower alkanol or lower alkenol, wherein the esterified hydroxy group has, e.g., the above given meaning, and stands, in particular, for halogen, e.g. chlorine, bromine or iodine, or organic sulphonyloxy, e.g. p-toluenesulphonyloxy. The reaction is performed preferably in the presence of a suitable base such as a tertiary amine, e.g. in the presence of a preferably sterically hindered tri-lower-alkylamine, such as ethyl-diisopropylamine (Hunig base). A methyl group $R_1$ can be introduced also by reaction with formaldehyde in the presence of formic acid.

The above reaction is performed, depending on the employed reagent, in the presence of a solvent or diluent and, if necessary, with cooling or heating, in a closed vessel and/or under an inert gas, e.g. in a nitrogen atmosphere.

The starting material of formula IV can be produced in a manner known per se, e.g. by reaction of a compound of formula II with an excess of ammonia. Furthermore, in a 2-(2-lower alkenyl)-, especially 2-allyl-5-R-2,3-dihydro-1H-dibenzo[2,3:6,7]thiepino[4,5-c]pyrrole or -dibenzo[2,3:6,7]ozepino[4,5-c]pyrrole, the N-2-loweralkenyl substituent, particularly the N-allyl substituent, can be replaced by an acyl group that can be split off, especially by a lower alkoxycarbonyl group, e.g. ethoxycarbonyl group, e.g. by treatment with a suitable acid halide, such as with a haloformic acid lower alkyl ester, e.g. chloroformic acid ethyl ester. In the thus obtainable 2-acyl-, such as 2-lower-alkoxy-carbonyl-, e.g. 2-ethoxycarbonyl-5-R-2,3-dihydro-1H-dibenzo[2,3:6,7]thiepino [4,5-c]pyrrole compound or -dibenzo[2,3:6,7]ozepino[4,5-c]pyrrole compound, the acyl group, such as the lower-alkoxy carbonyl group, e.g. ethoxycarbonyl group, is split off hydrolytically, e.g. by treatment with a suitable aqueous acid or basic agent such as aqueous hydrobromic acid or aqueous-ethanolic potassium hydroxide; or alcoholytically, e.g. by treatment with a lower alkanol such as ethanol, in the presence of an alkali metal hydroxide, e.g. potassium hydroxide, and thus replaced by hydrogen.

The new compounds of formula I wherein R stands for hydroxy can be produced also by a process in which, in a compound of the formula

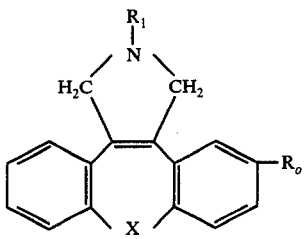

(V)

wherein $R_o$ represents a radical convertible into a hydroxy group, the group $R_o$ is converted into the free hydroxy group, and, optionally, the additional steps are carried out.

A suitable radical $R_o$ convertible into a free hydroxy group is, e.g., a functionally modified hydroxyl group. Such a group is usually a protected, especially etherified, but also esterified, hydroxy group different from the alkanoyloxy group R optionally present in the final materials. Such a group can be converted into the free hydroxy group, in a manner known per se, such as by means of solvolysis, e.g. hydrolysis, alcoholysis or acidolysis, or by means of reduction, e.g. hydrogenolytically, or by treatment with a chemical reagent, and also photolytically.

Etherified hydroxy groups $R_o$ are in general hydroxy groups etherified by organic radicals, principally by optionally substituted hydrocarbon radicals of an aliphatic character, or by partially or completely saturated heterocylic radicals. Such etherified hydroxy groups are, e.g., lower alkoxy, especially methoxy, as well as ethoxy, n-propyloxy-isopropyloxy or n-butyloxy, also tert.-lower alkoxy such as tert.-butyloxy or tert.-pentyloxy, aryl-lower-alkoxy such as optionally substituted α-phenyl-lower-alkoxy, e.g. benzyloxy or trityloxy, or 2-oxacycloalkoxy or 2-thiacycloalkoxy, e.g. 2-tetrahydrofuranyloxy, 2-tetrahydropyranyloxy or 2-thiacyclohexyloxy.

Esterified hydroxy groups $R_o$ are preferably esterified with an organic acid or with a semi-derivative or carbonic acid. Hydroxy groups esterified with an organic acid are acyloxy groups, wherein acyl denotes preferably the radical of some organic carboxylic acid, especially of an aliphatic, aromatic or araliphatic carboxylic or sulphonic acid; they are, inter alia, alkanoyloxy, e.g. lower-alkanoyloxy such as acetyloxy, propionyloxy or pivaloyloxy (such as a group $R_o$ can, if required, be present also as group R), aroyloxy, e.g. benzoyloxy, aryl-loweralkanoyloxy, e.g. phenylacetyloxy, lower-alkylsulphonyloxy, e.g. methylsulphonyloxy, or aryl-sulphonyloxy, e.g. 4-mthylsulphonyloxy. Hydroxy groups esterified with a semi-derivative of carbonic acid are esterified, in particular, by a semi-ester of carbonic acid wherein the esterifying moiety has aliphatic character, i.e. this moiety is bound by way of a carbon atom of aliphatic character with the oxygen atom of the carboxyl grouping of the carbonic acid. Hydroxy groups so esterified are, e.g. phenyl optionally substituted in the α-position of the esterifying moiety, e.g. by aryl, such as optionally, e.g., by lower alkyl such as tert.-butyl, hydroxy, lower alkoxy such as methoxy, nitro and/or phenyl; or phenyloxy substituted by aryloxy, such as optionally, e.g., by lower alkoxy such as methoxy; or benzoyl substituted by acyl, such as optionally, e.g., by halogen such as bromine; mono- or polysubstituted lower-alkoxycarbonyloxy; or lower-alkoxycarbonyloxy mono- or polysubstituted in the β-position of the esterifying moiety, e.g., by halogen such as chlorine, bromine or iodine. Hydroxy groups so esterified are, inner alia, lower-alkoxycarbonyloxy, e.g. methoxycarbonyloxy or ethoxycarbonyloxy, also tert.-lower-alkoxycarbonyloxy, e.g. tert.-butyloxycarbonyloxy or tert.-pentyloxycarbonyloxy, α-phenyl-loweralkoxy-carbonyloxy optionally containing lower alkoxy and/or nitro, e.g. benzyloxycarbonyloxy, 4-methoxybenzyloxycarbonyloxy, 4-nitro-benzyloxycarbonyloxy or 2-nitro-4,5-dimethoxybenzyloxycarbonyloxy, diphenyl-methoxycarbonyloxy optionally containing lower alkoxy, e.g. benzhydryloxycarbonyloxy, benzoylmethoxycarbonyloxy optionally containing halogen, e.g. phenacyloxycarbonyloxy, or 2-halo-lower alkoxycarbonyloxy, e.g. 2,2,2-trichloroethoxycarbonyloxy, 2-bromoethoxycarbonyloxy or 2-iodothoxycarbonyloxy.

The splitting off of a functionally modified hydroxy group $R_o$ can be performed in a manner known per se, usually by hydrolysis, if necessary in the presence of acid or basic agents, such as mineral acids, e.g. hydrochloric acid or hydrobromic acid (whereby the last-mentioned are suitable in particular for the splitting off of a lower-alkoxy group $R_o$, such as methoxy), or alkali metal hydroxides or alkali metal carbonates, e.g. sodium hydroxide or potassium hydroxide. Certain suitable etherified or esterified hydroxy groups can be split off also by means of other methods; thus, e.g., tert.-lower-alkoxy- or tert.-lower-alkoxycarbonyloxy, or diphenyl-methoxycarbonyloxy optionally containing lower alkoxy, by acidolysis (e.g. by treatment of the corresponding starting material with a suitable protonic, at most slightly nucleophilic, strong organic carboxylic or sulphonic acid, e.g. formic acid or trifluoroacetic acid), optionally substituted α-phenyl-lower-alkoxy or α-phenyl-lower-alkoxycarbonyloxy by hydrogenolysis (e.g. by treatment of the corresponding starting material with hydrogen in the presence of a metal catalyst suitable for hydrogenation purposes, such as palladium), 2-nitro-4,5-dimethoxy-benzyloxycarbonyloxy photolytically (e.g. by irradiation of the corresponding starting material with ultraviolet light, e.g. of a wave-length of above 290 mm), or benzoylmethoxycarbonyloxy optionally containing halogen of 2-halo-lower-alkoxycarbonyloxy by treatment with a chemical reducing agent (i.e. by means of nascent hydrogen, e.g. by treatment of the corresponding starting material with a suitable metal, e.g. zinc, or with a suitable metal salt, e.g. chromium-II-chloride, in the presence of of a hydrogen donor, e.g. aqueous acetic acid, whereby, e.g., a 2-bromoethoxycarbonyloxy is converted, before the treatment with the chemical reducing agent, advantageously, e.g., by treatment with a suitable iodine salt, such as sodium iodide, into the 2-iodoethoxycarbonyloxy group).

The above-splitting-off-reaction is usually performed in the presence of a solvent or diluent or of a mixture thereof; the splitting-off reagent used in excess can simultaneously also serve as solvent or diluent. Furthermore, the reaction is performed, if necessary or if desired, with cooling or heating, e.g. in a temperature range of about −10° C to about 120° C, in a closed vessel under pressure and/or in an inert gas atmosphere, e.g. in a nitrogen atmosphere.

A further radical convertible into the hydroxy group $R_o$ is the amino group, which can be converted into the hydroxy group, in a manner known per se, by diazotising, e.g. by treatment with nitrous acid in an acid medium, e.g. in the presence of a mineral acid, such as hydrochloric acid or sulphuric acid, and usually water, whereby also suitable nitrite salts such as alkali metal nitrites, e.g. sodium nitrite, can be used, or by treatment with a nitrosyl halide, e.g. nitrosyl chloride, or with an organic nitrite, e.g pentyl nitrite, in the presence of an inert solvent, and subsequent hydrolysis of the thus obtainable diazonium compound with water, optionally in the presence of an acid such as a mineral acid, and optionally with the addition of a suitable catalyst, e.g. copper sulphate, and/or with heating, e.g. up to approx. 80° C, whereby the hydrolysis can take place directly in the diazotising mixture.

The starting materials of formula V are known or can be produced in a manner known per se, e.g. by a process in which a compound of the formula

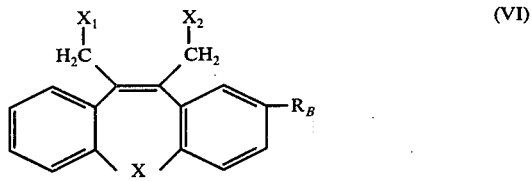

wherein $X_1$ and $X_2$ have the above-given meanings, and $R_B$ represents the radical $R_o$ or a radical convertible into this, is reacted with an amine of the formula $R_1$-$NH_2$ (III), and, if necessary or required, in a compound thus obtained, the group $R_B$ is converted into the radical $R_o$.

The groups $X_1$ and $X_2$ stand in particular for halogen and especially for bromine, while $R_B$ preferably stands for $R_o$ and particularly for lower alkoxy, e.g. methoxy, but also, e.g., for a protected amine group such as an acylated amino group, wherein the acyl radical represents, e.g., one of the corresponding radicals which occur in an acyyloxy radical $R_o$.

The reaction of a compound of formula VI with an amine of formula III can be carried out, e.g., in the manner described above for the reaction of a compound of formula II with a compound of formula III. If necessary, a group $R_B$ is converted in a resulting compound, e.g. an acylated amino group $R_B$ such as a lower-alkanoylamino group, in a manner known per se, e.g. by hydrolysis in an acid or alkali medium, into a group $R_o$, e.g. into the free amino group.

In a compound of formula I obtainable according to the process, an alkanoyloxy group R can be converted in a manner known per se, e.g. by solvolysis such as hydrolysis or alcoholysis, optionally in the presence of a basic or acid agent such as an aqueous alkali metal hydroxide, e.g. sodium or potassium hydroxide, into the free hydroxy group R. Alternatively, it is possible to convert in a compound obtainable by the process the free hydroxy group R into an alkanoyloxy group R by acylation, e.g. by treatment with a symmetrical or mixed anhydride of an alkanecarboxylic acid, such as with an alkanecarboxylic acid halide, e.g chloride, usually in the presence of a basic agent such as an inorganic base, e.g. an agent forming phenolate, such as an alkali metal, e.g. sodium or potassium, or a suitable alkali metal compound, e.g. a sodium or potassium compound, such as a suitable hydride, amide or hydroxide, or a suitable organic nitrogen base such as diisopropylethylamine or pyridine, including a quaternary ammonium base.

Depending on the conditions of the process and on the starting materials, there are obtained optionally salt-forming final materials in the free form or in the form of their salts which can be converted in the usual manner into each other or into other salts. Thus, free compounds of formula I are formed from resulting acid addition salts, e.g. by treatment with bases or with basic ion exchangers, whereas free bases of formula I are converted into acid addition salts, e.g. by reaction with organic or inorganic acids, especially with those that are suitable for the formation of pharmaeutically applicable salts, such as the aforementioned.

Salts of the new compounds can also be used for purification purposes, e.g. by a process wherein the free compounds are converted into their salts, these are isolated and optionally purified, and again converted into the free compounds. In consequence of the close relationship between the new compounds in the free form and in the form of their salts, it is to be taken, in the foregoing and in the following, that by the term 'free compounds' is meant, where the case applies and with the appropriate modifications, also the corresponding salts.

The invention relates also to those modifications of the process whereby a compound occurring as an intermediate at some stage is used as the starting material, and the uncompleted steps are performed, or whereby the process is interrupted at some stage, or whereby a starting material is formed under the reaction conditions, or whereby a reaction constituent is optionally present in the form of its salts.

For the carrying out of the process according to the invention, there are advantageously used such starting materials which yield the initially specially mentioned groups of final products, and particularly the specifically described or emphasised final materials.

The new compoiunds can be used, e.g., in the form of pharmaceutical preparations which contain an effective amount of the active substance, optionally together with inorganic or organic, solid or liquid, pharmaceutically usable carrier substances suitable for enteral, e.g. oral, or parenteral administration. There are thus used tablets or gelatine capsules containing the active substance together with extenders, e.g. lactose, dextrose, sucrose, mannitol, sorbitol, cellulose and/or glycin, and lubricants, e.g. diatomaceous earth, talcum, stearic acid or salts thereof, such as magnesium or calcium stearate, and/or polyethylene glycol; tablets contain also binding agents, e.g. magnesium aluminium silicate, starches such as maize, wheat, rice or arrowroot starch, gelatine, tragacanth, methylcellulose, sodium carboxymethylcellulose and/or polyvinylpyrrolidone, and, optionally, effervescent agents, e.g. starches, agar, alginic acid or a salt thereof, such as sodium alginate, and/or effervescent mixtures, or adsorption agents, colouring agents, flavouring agents and sweetening agents. Furthermore, the new pharmacologically effective compounds can be used in the form of injectable preparations, e.g. intravenously administered preparations, or in the form of infusion solutions. Such solutions are preferably isotonic aqueous solutions or suspensions; these can be prepared before use, e.g. as lyophilised preparations containing the active substance alone or together with a carrier material, e.g. mannitol. The pharmaceutical preparations can be sterilised and/or contain auxiliaries, e.g. preservatives, stabilising agents, wetting and/or emulsifying agents, solubility-promoting agents, salts for regulation of the osmotic pressure, and/or buffers. The present pharmaceutical preparations, which can optionally contain further pharmacologically valuable substances, are produced in a manner known per se, e.g.

by means of conventional mixing, granulating, coating, solution or lyophilising processes, and they contain from about 0.1% to 100%, especially from about 1% to 50%, of lyophilisates to up to 100% of active substance. The dosage amounts depend on the mode of application, on the species, on the age and on the individual condition. The daily doses of the free base or of pharmaceutically acceptable salts thereof vary between about 0.05 g and 0.3 g for warm-blooded animals having a weight of about 70 kg.

The following examples serve to illustrate the invention; temperatures are given in degrees Centigrade.

EXAMPLE 1

A mixture of 23.0 g of 2-methyl-5-methoxy-2,3-dihydro-1H-dibenzo[2,3:6,7]thiepino[4,5-c]pyrrole and 115 ml of 48% aqueous hydrobromic acid is refluxed for 3 hours with stirring, and then cooled to 20°. The precipitated hydrobromide of 2-methyl-5-hydroxy-2,3-dihydro-1H-dibenzo[2,3:6,7]thiepino[4,5-c]pyrrole is filtered off and dissolved in 250 ml of 60% aqueous methanol. The solution is rendered alkaline by addition of concentrated aqueous ammonia solution (phenolphthalein), whereupon free 2-methyl-5-hydroxy-2,3-dihydro-1H-dibenzo[2,3:6,7]thiepino [4,5-c]pyrrole crystallises out. The product melts at 242°–245° after recrystallisation from methanol.

EXAMPLE 2

A suspension of 14.5 g of 2-methyl-5-hydroxy-2,3-dihydro-1H-dibenzo[2,3:6,7]thiepino[4,5-c]pyrrole in a mixture of 50 ml of absolute ethanol and 100 ml of acetone is made neutral with 4.95 g of methanesulphonic acid, whereupon the base goes into solution, and after some time the methanesulphonic acid salt of 2-methyl-5-hydroxy-2,3-dihydro-1H-dibenzo[2,3:6,7]thiepino[4,5-c]pyrrole crystallises out. The salt melts at 194°– 195° after recrystallisation from absolute ethanol.

EXAMPLE 3

By boiling 11 g of 2-ethyl-5-methoxy-2,3-dihydro-1H-dibenzo[2,3:6,7]thiepino[4,5-c]pyrrole in 55 ml of 48% aqueous hydrobromic acid there is obtained, by a process analogous to that described in Example 1, 2-ethyl-5-hydroxy-2,3-dihydro-1H-dibenzo[2,3:6,7]-thiepino[4,5-c]pyrrole, which melts at 224°–227° after recrystallisation from ethanol. The methanesulphonic acid salt of 2-ethyl-5-hydroxy-2,3-dihydro-1H-dibenzo[2,3:6,7]thiepino[4,5-c]pyrrole is obtained by a procedure analogous to that of Example 2; it melts at 252°–255° after recrystallisation from 80% ethanol.

EXAMPLE 4

By boiling 14 g of 2-methyl-5-methoxy-2,3-dihydro-1H-dibenzo[2,3:6,7]oxepino[4,5-c]pyrrole in 70 ml of 48% aqueous hydrobromic acid there is obtained, by a process analogous to that described in Example 1, 2-methyl-5-hydroxy-2,3-dihydro-1H-dibenzo[1,2:6,7]oxepino[4,5-c]pyrrole, which melts at 244°–250° after recrystallisation from methanol. The methanesulphonic acid salt of 2-methyl 5-hydroxy-2,3-dihydro-1H-dibenzo[2,3:6,7]oxepino[4,5-c]pyrrole is obtained by a procedure analogous to that of Example 2; it melts at 235°–238° after recrystallisation from methanol.

EXAMPLE 5

By boiling 14.7 g of 2-ethyl-5-methoxy-2,3-dihyro-1H-dibenzo[2,3-6,7]oxepino[4,5-c]pyrrole in 73.5 ml of 48% aqueous hydrobromic acid there is obtained, by a method analogous to that described in Example 1, 2-ethyl-5-hydroxy-2,3-dihydro-1H-dibenzo[2,3:6,7]oxepino[4,5-c]pyrrole, which melts at 172°–174° after recrystallisation from methanol. The methanesulphonic acid salt of 2-ethyl-5-hydroxy-2,3-dihydro-1H-dibenzo[2,3:6,7]oxepino[4,5-c]pyrrole is obtained by a process analogous to that of Example 2: it melts at 219°–222° after recrystallisation from ethanol.

EXAMPLE 6

A solution of 4.7 g of acetyl chloride in 20 ml of absolute benzene is added dropwise within one hour, with stirring, to a solution of 8.4 g of 2-methyl-5-hydroxy-2,3-dihydro-1H-dibenzo[2,3:6,7]thiepino[4,5-c]pyrrole in 150 ml of absolute pyridine, with the temperature being maintained at between 0° and 5°. Stirring is subsequently continued for 2 hours at room temperature; the reaction mixture is then poured on ice water and extracted with ether. The ether solution is separated, washed with water and, after drying over sodium sulphate, concentrated by evaporation, whereupon 2-methyl-5-acetoxy-2,3-dihydro-1H-dibenzo[2,3:6,7-thiepino[4,5-c]pyrrole is obtained as oil.

9.5 g of the oily crude base is dissolved in 50 ml of acetone, and neutralized with a solution of 2.7 g of anhydrous oxalic acid in 10 ml of absolute ethanol, whereupon the oxalate crystallises out; this melts at 117°–120° after crystallisation from abs. ethanol/abs.ether.

EXAMPLE 7

The following final products are produced analogously to Example 6:

a. from 5.6 g of 2-methyl-5-hydroxy-2,3-dihydro-1H-dibenzo[2,3:6,7]-thiepino[4,5-c]pyrrole in 120 ml of absolute pyridine and 5.9 g of heptanoyl chloride in 10 ml of abs. benzene:- 2-methyl-5-heptanoyloxy-2,3-dihydro-1H-dibenzo[2,3:6,7]thiepino[4,5-c]pyrrole, the oxalate of which melts at 195°–197° after recrystallisation from abs. ethanol.

b. from 5.6 g of 2-ethyl-5-hydroxy-2,3-dihydro-1H-dibenzo [2,3:6,7]oxepino[4,5-c]pyrrole in 120 ml of absolute pyrridine and 3.1 g of acetyl chloride in 10 ml of abs. benzene:- 2-ethyl-5-acetoxy-2,3-dihydro-1H-dibenzo[2,3:6,7]oxepino[4,5-c]pyrrole, the oxalate of which melts at 152°–155° after recrystallisation from abs. ethanol/acetone.

EXAMPLE 8

Tablets containing 0.02 g of the methanesulphonic acid salt of 2-methyl-5-hydroxy-2,3-dihydro-1H-dibenzo[2,3:6,7]thiepino[4,5-c]pyrrole are produced as follows:

| Composition (for 10000 tablets) | |
|---|---|
| methanesulphonic acid salt of 2-methyl-5-hydroxy-2,3-dihydro-1H-dibenzo[2,3:6,7]thiepino[4,5-c]pyrrole | 200.00 g |
| lactose | 200.80 g |
| potato starch | 354.70 g |
| stearic acid | 10.00 g |
| talcum | 200.00 g |
| magnesium stearate | 2.50 g |
| colloidal silicon dioxide | 32.00 g |
| ethanol | q.s. |

A mixture of the methanesulphonic acid salt of 2-methyl-5-hydroxy-2,3-dihydro-1H-dibenzo[2,3:6,7]- thiepino[4,5-c]pyrrole, the lactose and 194.70 g of potato starch is moistened with an ethanolic solution of stearic acid and then granulated through a sieve. The granulate is dried and the remaining potato starch, the talcum, the magnesium stearate and the colloidal silicon dioxide are mixed in, and the mixture is pressed to form tablets each weighing 0.1 g. which can optionally be provided with grooves for a finer adjustment of the dosage amount.

EXAMPLE 9

Dragées containing 0.02 g of the methanesulphonic acid salt of 2-methyl-5-hydroxy-2,3-dihydro-1H-dibenzo [2,3:6,7]thiepino[4,5-c]pyrrole are produced as follows:

| Composition (for 10,000 dragées) | |
|---|---|
| methanesulphonic acid salt of 2-methyl-5-hydroxy-2,3-dihydro-1H-dibenzo[2,3:6,7]thiepino[4,5-c]pyrrole | 100.00 g |
| lactose | 175.90 g |
| stearic acid | 10.00 g |
| colloidal silicon dioxide | 56.60 g |
| talcum | 165.00 g |
| potato starch | 20.00 g |
| magnesium stearate | 2.50 g |
| saccharose (cryst.) | 502.28 g |
| shellac | 6.00 g |
| gum arabic | 10.00 g |
| dyestuff | 0.22 g |
| titanium dioxide | 1.50 g |
| ethanol | q.s. |

A granulate is produced from 2-methyl-5-hydroxy-2,3-dihydro-1H-dibenzo[2,3:6,7]thiepino[4,5-c]pyrrole, lactose and an ethanolic solution of stearic acid; and, after drying, the granulate is mixed with colloidal silica dioxide, talcum, potato starch and magnesium stearate, and the mixture is pressed to form dragee cores. These are subsequently coated with a concentrated syrup made from saccharose, shellac, gum arabic, dyestuff and titanium dioxide to thus obtain dragees each weighing 0.105 g.

EXAMPLE 10

Capsules containing 0.02 g of the methanesulphonic acid salt of 2-methyl-5-hydroxy-2,3-dihydro-1H-dibenzo [2,3:6,7]thiepino[4,5-c]pyrrole are produced as follows:

| Composition for 1000 capsules: | |
|---|---|
| Methanesulphonic acid salt of 2-methyl-5-hydroxy-2,3-dihydro-1H-dibenzo[2,3:6,7]thiepino[4,5-c]pyrrole | 20.00 g |
| lactose | 253.00 g |
| gelatine | 2.00 g |
| maize starch | 10.00 g |
| talcum | 15.00 g |
| water | q.s. |

The methanesulphonic acid salt of 2-methyl-5-hydroxy-2,3-dihydro-1H-dibenzo[2,3:6,7]thiepino[4,5-c]pyrrole is mixed with lactose, the mixture is uniformly moistened with an aqueous solution of gelatine, and is then granulated through a suitable sieve (e.g. Sieve III according to Ph.Helv. V). The granulate is mixed with the dried maize starch and talcum, and the mixture is evenly filled into hard gelatine capsules (size 1).

EXAMPLE 11

An aqueous injection solution containing 0.01 g/ml of the methanesulphonic acid salt of 2-methyl-5-hydroxy-2,3-dihydro-1H-dibenzo[2,3:6,7]thiepino[4,5-c]pyrrole is produced as follows:

| Composition (for 1000 ampoules): | |
|---|---|
| methanesulphonic acid salt of 2-methyl-5-hydroxy-2,3-dihydro-1H-dibenzo[2,3:6,7]thiepino[4,5-c]pyrrole | 10.00 g |
| water | q.s. |

A solution of the methanesulphonic acid salt of 2-methyl-5-hydroxy-2,3-dihydro-1H-dibenzo[2,3:6,7]-thiepino[4,5-]pyrrole in 1000 ml of water is filled into ampoules and sterilised. An ampoule contains a 1% solution of the active substance.

EXAMPLE 12

Also the following compounds can be used as active substance for tablets, dragees, capsules, suppositories, ampoules, etc.:

2-ethyl-5-hydroxy-2,3-dihydro-1H-dibenzo[2,3:6,7]-thiepino [4,5-c]pyrrole or a salt, e.g. the methanesulphonic acid salt thereof;

2-methyl-5-acetoxy-2,3-dihydro-1H-dibenzo[2,3:6,7]-thiepino [4,5-c]pyrrole or a salt thereof; and 2-methyl-5-heptanoyloxy-2,3-dihydro-1H-dibenzo[2,3:6,7]thiepino[4,5-c]pyrrole or a salt thereof.

What is claimed is:

1. 5-Oxygenated asatetracyclic compounds substituted in the 1-position which correspond to the formula wherein X represents oxygen or sulphur, R represents a hydroxy group, and $R_1$ stands for lower alkyl, or acid addition salts thereof.

2. Compounds of formula I according to claim 1, wherein X stands for sulphur, R for hydroxy, and $R_1$ for lower alkyl having up to 4 carbon atoms or acid addition salts thereof.

3. Compounds of formula I according to claim 1, wherein X stands for sulphur, R for hydroxy and $R_1$ for methyl or ethyl or acid addition salts thereof.

4. A compound of formula I according to claim 1 which is 2-Methyl-5-hydroxy-2,3-dihydro-1H-dibenzo[2,3:6,7]thiepino [4,5-c]pyrrole or acid addition salts thereof.

5. The hydrobromide salt of the compound of claim 4.

6. The methanesulphonic acid salt of the compound of claim 4.

7. A compound of formula I according to claim 1 which is 2-Ethyl-5-hydroxy-2,3-dihydro-1H-dibenzo[2,3:6,7]thiepino [4,5-c]pyrrole or acid addition salts thereof.

8. The hydrobromide salt of the compound of claim 7.

9. The methanesulphonic acid salt of the compound of claim 7.

10. A compound of formula I according to claim 1 which is 2-methyl-5-hydroxy-2,3-dihydro-1H-dibenzo[2,3:6,7]oxepino[4,5-c]pyrrole or acid addition salts thereof.

11. The hydrobromic salt of the compound of claim 10.

12. The methanesulphonic acid salt of the compound of claim 10.

13. A compound of formula I according to claim 1 which is 2-ethyl-5-hydroxy-2,3-dihydro-1H-dibenzo[2,3:6,7]oxepino [4,5-c]pyrrole or acid addition salts thereof.

14. The hydrobromic salt of the compound of claim 13.

15. The methanesulphonic acid salt of the compound of claim 13.

16. Pharmaceutically applicable non-toxic acid addition salts of a compound of formula I according to claim 1.

17. A pharmaceutical preparation for the treatment of tension and agitation which comprises a therapeutically effective amount of a compound of formula I according to claim 1 or a pharmaceutically applicable acid addition salt thereof, together with a pharmaceuticaly usable carrier material.

18. A method for the treatment of tension and agitation by administration of a therapeutically effective amount of a compound of formula I according to claim 1 or a pharmaceutically applicable acid addition salt thereof, together with a pharmaceutically usable carrier material.

* * * * *